United States Patent
Chiou et al.

(10) Patent No.: US 9,237,998 B2
(45) Date of Patent: *Jan. 19, 2016

(54) CARRIER SYSTEM FOR WATER-SOLUBLE ACTIVE INGREDIENTS

(71) Applicant: L'OREAL, Paris (FR)

(72) Inventors: Catherine Chiou, Saddle Brook, NJ (US); Zhi Pan, Fort Lee, NJ (US); Angelike Galdi, Westfield, NJ (US); Lauren E. Manning, Hoboken, NJ (US); Andrew Goldberg, Clark, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/136,634

(22) Filed: Dec. 20, 2013

(65) Prior Publication Data
US 2015/0174047 A1 Jun. 25, 2015

(51) Int. Cl.
| | |
|---|---|
| *A61K 8/89* | (2006.01) |
| *A61Q 19/08* | (2006.01) |
| *A61K 8/891* | (2006.01) |
| *A61K 8/365* | (2006.01) |
| *A61K 8/368* | (2006.01) |
| *A61K 8/49* | (2006.01) |
| *A61K 8/60* | (2006.01) |

(52) U.S. Cl.
CPC .................. *A61K 8/891* (2013.01); *A61K 8/365* (2013.01); *A61K 8/368* (2013.01); *A61K 8/494* (2013.01); *A61K 8/498* (2013.01); *A61K 8/4926* (2013.01); *A61K 8/4953* (2013.01); *A61K 8/4973* (2013.01); *A61K 8/60* (2013.01); *A61K 8/89* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 4,268,499 A | 5/1981 | Keil | |
| 4,917,882 A | 4/1990 | Strobridge | |
| 5,601,811 A | 2/1997 | Gallagher et al. | |
| 6,524,598 B2 | 2/2003 | Sunkiel et al. | |
| 6,696,049 B2 | 2/2004 | Vatter et al. | |
| 7,262,217 B2 | 8/2007 | Baranger et al. | |
| 8,216,555 B2 | 7/2012 | Nieuwenhuijsen | |
| 8,299,127 B2 | 10/2012 | Anjing et al. | |
| 8,461,206 B2 | 6/2013 | Dalko | |
| 8,481,594 B2 | 7/2013 | Boulle et al. | |
| 8,603,502 B2 | 12/2013 | Boulle et al. | |
| 8,609,117 B2 | 12/2013 | Boulle et al. | |
| 2003/0064046 A1 | 4/2003 | Omura et al. | |
| 2007/0128137 A1 | 6/2007 | Yoshimi | |
| 2007/0264210 A1 | 11/2007 | Robinson | |
| 2008/0014162 A1* | 1/2008 | Willemin et al. | ............. 424/70.1 |
| 2008/0153839 A1* | 6/2008 | Cotton et al. | ............ 514/252.12 |
| 2009/0035236 A1* | 2/2009 | Maes et al. | ....................... 424/59 |
| 2010/0179222 A1 | 7/2010 | Boulle et al. | |
| 2010/0310617 A1 | 12/2010 | Zhang et al. | |
| 2011/0256077 A1 | 10/2011 | Hayakawa | |
| 2012/0088836 A1 | 4/2012 | Dalko | |
| 2012/0322876 A1 | 12/2012 | Kermorvan et al. | |
| 2013/0142740 A1 | 6/2013 | Cziryak et al. | |
| 2013/0345317 A1 | 12/2013 | Chiou | |
| 2014/0308323 A1* | 10/2014 | Midha et al. | .................. 424/401 |

FOREIGN PATENT DOCUMENTS

| | | |
|---|---|---|
| CN | 1793822 A | 6/2006 |
| DE | 102009045981 A1 | 8/2010 |
| EP | 1027883 A2 | 8/2000 |
| EP | 1671680 A1 | 6/2006 |
| EP | 1990372 A2 | 11/2008 |
| EP | 2016932 A2 | 1/2009 |
| EP | 2319484 A2 | 5/2011 |
| FR | 2847469 A1 | 5/2004 |
| FR | 2847470 A1 | 5/2004 |
| FR | 2909552 A1 | 6/2008 |
| FR | 2921254 A1 | 3/2009 |
| FR | 2921255 A1 | 3/2009 |
| FR | 2940053 A1 | 6/2010 |
| FR | 2951375 A1 | 4/2011 |
| FR | 2953718 A1 | 6/2011 |
| FR | 2954122 A1 | 6/2011 |
| FR | 2964865 A1 | 3/2012 |

(Continued)

OTHER PUBLICATIONS

Kawada et al, Evaluation of anti-wrinkle effects of a novel cosmetic containing niacinamide, Journal of Dermatology 2008; 35:637-642.*
U.S. Appl. No. 14/136,471, filed Dec. 20, 2013, Chiou.
U.S. Appl. No. 14/136,562, filed Dec. 20, 2013, Galdi.
U.S. Appl. No. 14/136,634, filed Dec. 20, 2013, Chiou.
U.S. Appl. No. 14/136,714, filed Dec. 20, 2013, Chiou.

(Continued)

*Primary Examiner* — Jennifer A Berrios

(74) *Attorney, Agent, or Firm* — McNees Wallace & Nurick LLC

(57) ABSTRACT

A water releasing composition in the form of an emulsion and process for using the composition are provided. The composition includes an aqueous phase and an oil phase. The aqueous phase includes at least one water-soluble active ingredient at a concentration by weight of from about 0.1% to about 20%, based upon weight of the composition. The oil phase includes dimethicone at a concentration by weight of about 1% to about 25%, and an emulsifying crosslinked siloxane elastomer at a concentration by weight of about 0.1% to about 20%, both based upon weight of the composition. The composition has a phase ratio of the aqueous phase to the oil phase of about 3.0 to about 12.0. The composition converts from an emulsion to a plurality of droplets upon application of shear.

14 Claims, No Drawings

(56) References Cited

FOREIGN PATENT DOCUMENTS

| | | | |
|---|---|---|---|
| FR | 2973693 | A1 | 10/2012 |
| FR | 2977478 | A1 | 1/2013 |
| FR | 2988291 | A1 | 9/2013 |
| FR | 2988292 | A1 | 9/2013 |
| JP | 2001205061 | A | 7/2001 |
| VN | PCT/US2013/045613 | | 6/2013 |
| WO | 0069423 | A1 | 11/2000 |
| WO | 0024365 | A1 | 1/2009 |
| WO | 2010000584 | A2 | 1/2010 |
| WO | 2011054600 | A1 | 5/2011 |
| WO | 2012084699 | A2 | 6/2012 |
| WO | 2012084701 | A2 | 6/2012 |
| WO | 2012136564 | A2 | 10/2012 |
| WO | 2012136818 | A2 | 10/2012 |
| WO | 2012143645 | A2 | 10/2012 |
| WO | 2013007637 | A2 | 1/2013 |
| WO | 2013007647 | A1 | 1/2013 |
| WO | 2013192004 | A2 | 12/2013 |

OTHER PUBLICATIONS

U.S. Appl. No. 13/529,113, Jun. 21, 2012, Chiou.
U.S. Appl. No. 13/529,059, Jun. 21, 2012, Chiou.
U.S. Appl. No. 13/855,495, filed Apr. 2, 2013, Chiou.
C. Tran, J.F. Michelet, L. Simonetti, F. Fiat, A. Garrigues, A. Potter, E. Segot, R.E.B. Watson, C.E.M. Griffiths, O. De Lacharriere, in vitro and in vivo studies with tetra-hydro-jasmonic acid (LR2412) reveal its potential to correct signs of skin ageing, Journal of the European Academy of Dermatology and Venereology 2013 European Academy of Dermatology and Venereology, p. 1-9, DOI: 10.1111/jdv.12113.
M. Vonka, J. Kosek, Modelling the morphology evolution of polymer materials undergoing phase separation, Chemical Engineering Journal, 2012, p. 1-11, http://dx.doi.org/10.1016/j.cej.2012.06.091.

* cited by examiner

CARRIER SYSTEM FOR WATER-SOLUBLE ACTIVE INGREDIENTS

FIELD OF THE INVENTION

The present invention is directed to compositions containing water-soluble active ingredients and methods of using them. More specifically, the present invention is directed to a composition in the form of an emulsion having an aqueous phase including at least one water-soluble active ingredient and an oil phase containing dimethicone and an emulsifying crosslinked siloxane elastomer. The composition is capable of carrying high amounts of water-soluble ingredients in a texturally pleasing manner, without experiencing separation of the emulsion. The present invention also provides a water-releasing effect when applied onto a keratinous substrate such as skin, hair or nails. The water-releasing effect enables the composition, initially in the form of an emulsion, to be converted into a plurality of droplets upon application of shear such as, for example, rubbing.

BACKGROUND OF THE INVENTION

The incorporation of water-soluble active ingredients into emulsion-type compositions has posed various stability challenges. This has been especially true when the desire was to incorporate larger amounts of said ingredients into compositions. Examples of lack of stability include discoloration of the formula and/or precipitation of the ingredients out of the composition. It is therefore an object of the present invention to provide a composition capable of stably carrying water-soluble active ingredients, which is also tactilely pleasing to consumers upon application.

BRIEF DESCRIPTION OF THE INVENTION

All numbers expressing quantities of ingredients and/or reaction conditions are understood as being modified in all instances by the term "about", unless otherwise stated.

In an exemplary embodiment, a composition in the form of a stable, tactilely pleasing emulsion containing significant amounts of at least one water-soluble active ingredient is provided. The composition includes an aqueous phase and an oil phase. The aqueous phase contains at least one water-soluble ingredient at a concentration of from about 0.1% to about 20% by weight, based upon the total weight of the composition. The oil phase contains dimethicone at a concentration by weight of from about 1% to about 25%, based upon the total weight of the composition, and an emulsifying crosslinked siloxane elastomer at a concentration by weight of from about 0.1% to about 20%, based upon the total weight of the composition. The skin care composition has a phase ratio of aqueous phase to oil phase of from about 3 to about 12. The composition converts from an emulsion to a plurality of droplets upon application of force such as, for example, rubbing with one's fingers or using an electromechanical force-imparting device such as, for example, an electromechanical cleansing brush.

In another exemplary embodiment, a method of delivering skin care active ingredients on keratinous substrates is provided. The method includes applying the above-disclosed composition onto the surface of a keratinous substrate, followed by application of force onto the composition present on the keratinous substrate.

Other features and advantages of the present invention will be apparent from the following more detailed description of the preferred embodiment which illustrates, by way of example, the principles of the invention.

DETAILED DESCRIPTION OF THE INVENTION

"Keratinous substrate," as used herein, includes but is not limited to skin, hair, and nails.

"Force", as used herein, includes shear/friction produced by a rubbing motion of an end user's fingers, an electromechanical cleansing device having a movable brush with bristles, and/or an electromechanical device that produces a tapping motion, similar to one's fingers tapping on the surface of the skin.

"Homogenous" means substantially uniform throughout, i.e., a single phase mixture.

In the present application the term "ambient temperature" means a temperature of about 25° C.

In the present application the term "stable" means the emulsion remains intact without phase separation, color and/or odor change over the stability monitoring period and the water-soluble active ingredients remain solubilized in the water phase without crystallization or precipitation out of the emulsion.

In the present application the term "water releasing," as used herein, describes the phenomenon wherein, after application of a composition onto a target substrate, force is then applied onto the composition causing the water-in-oil type emulsion to rupture, which in turn causes the internal aqueous phase containing the water-soluble ingredient(s) to emerge in the form of droplets.

The anti-aging composition and method of the present invention can comprise, consist of, or consist essentially of the essential elements and limitations of the invention described herein, as well as any additional or optional ingredients, components, or limitations described herein or otherwise useful in compositions intended for topical application onto keratinous substrates.

It has been surprisingly discovered by the inventors that high concentrations of water-soluble active ingredients such as, for example, phenolic or polyphenolic acids, can be formulated into a stable water-in-oil type emulsion which, though initially in the form of a cream, possesses a transformative water-releasing effect upon application of force such as, for example, shear. The transformative water-releasing effect is that the cream transforms into droplets containing the aqueous phase with the water-soluble ingredient which, when exposed to force such as the shearing effect caused by rubbing/massaging the emulsion present on the surface of the keratinous substrate, thereby forcing the water-soluble ingredient containing droplets into the keratinous substrate.

One advantage of an embodiment of the present disclosure includes providing a stable composition capable of carrying relatively high levels of electrolytic water-soluble ingredients without undergoing phase separation, i.e. breaking the emulsion. Yet another advantage of an embodiment of the present disclosure is providing a skin care or cosmetic composition capable of producing a water-releasing effect onto a keratinous substrate, such as skin. The water-releasing effect enables the composition, initially in the form of an emulsion, to be converted into a plurality of droplets carrying high levels of water-soluble ingredients upon application of force such as, for example, shear caused by an end user's rubbing of the composition onto the surface of a target keratinous substrate. The droplets, in turn, enable the water-soluble ingredients present in said droplets to effectively penetrate into a target keratinous substrate.

The water-in-oil emulsion system of the present invention typically has a white, glossy cream appearance. However, it may be modified so as to have a transparent gel-like or matte appearance by adjusting its refractive index. When the composition is deposited onto a target keratinous substrate, followed by application of force, the composition quickly releases the aqueous phase containing the water-soluble ingredients in the form of bead-like droplets, thereby enabling the water-soluble ingredients present in the aqueous phase to be forced into the surface of the target keratinous substrate.

Aqueous Phase

The aqueous phase present in the composition according to the disclosure includes at least one water soluble ingredient, water, and other aqueous phase ingredients. The aqueous phase of the composition is at a concentration, by weight, of from about 60% to about 92%, or alternatively from about 70% to about 90%, or alternatively from about 80% to about 90% based upon weight of the composition.

Water-Soluble Active Ingredient

The aqueous phase present in the composition according to the disclosure includes at least one water-soluble active ingredient at a concentration, by weight, of from about 0.1% to about 20%, or alternatively from about 0.1% to about 15%, or alternatively from about 0.5% to about 10% based upon weight of the composition.

In one embodiment, where the water-soluble active ingredient is ellagic acid, the preferred concentration, by weight, is from about 0.001% to about 0.01%, due to the inherently low water solubility of ellagic acid.

The water-soluble active ingredients can be present in their synthetic chemical compound forms, or alternatively as integral part of botanical extracts. Suitable examples of water-soluble ingredients, include, but not limited to, (1) phenolic and polyphenolic compounds, and (2) other non-phenolic compounds.

Phenolic and polyphenolic compounds include, but not limited to, flavones, chalcones, tannins, phenolic acids, catechins, anthocyanidins, stilbenoids, curcuminoids, phenylpropanenoids. Many of phenolic and polyphenolic compounds are well-known antioxidants and/or compounds that can provide skin care and cosmetic benefits. Some popular examples are baicalin, resveratrol, ferulic acid, ellagic acid, salicylic acid, and botanical extracts.

Other non-phenolic, water-soluble compounds include, but to, vitamins, ceramides, not limited xanthines, cholesterols, sphingosines, C-glycosides, zwitterionic N-substituted amino sulfonic acid buffers, sugars, nucleic acids, α- and β-hydroxy acids, botanical extracts, aminopropyl triethoxysilane (APTES), dihydroxyacetone (DHA), amino acids, and peptides, and their derivatives and mixtures thereof.

Optional Hydrotropes

The composition of the present disclosure may optionally include hydrotropes. Examples of suitable hydrotropes include, for example, but not limited to, nicotinamide, caffeine, sodium PCA, sodium salicylate, urea, or hydroxyethyl urea. At least one or a combination of two or more hydrotropes can be used to improve the solubility of phenolic and polyphenolic compounds in the water phase.

Hydrotropes may be present in the compositions in amounts generally ranging from about 0.1% to about 20% by weight, preferably from about 0.5% to about 10% by weight, and most preferably from about 1% to about 5% by weight, based on the total weight of the composition.

Water

The aqueous phase present in the composition according to the disclosure includes water at a concentration by weight of about 60% to about 92%, or alternatively about 70% to about 90% or alternatively about 80% to about 90%, based upon the total weight of the composition. The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

Oil Phase

The oil phase present in the composition according to the disclosure includes dimethicone and an emulsifying crosslinked siloxane elastomer. The oil phase of the water-releasing composition is at a concentration by weight of about 8% to about 25%, or alternatively about 10% to about 20%, or alternatively about 10% to about 15%, based upon the total weight of the composition.

Dimethicone

The oil phase present in the composition according to the disclosure includes dimethicone at a concentration, by weight, of about 1% to about 25%, or alternatively about 2% to about 20%, or alternatively about 4% to about 15%, based upon weight of the composition.

Emulsifying Crosslinked Siloxane Elastomer

The oil phase present in the composition according to the disclosure includes an emulsifying crosslinked siloxane elastomer at a concentration, by weight, of about 0.1% to about 20%, or alternatively about 0.3% to about 10%, or alternatively about 0.5% to about 7%, based upon weight of the composition.

Examples of suitable emulsifying crosslinked siloxane elastomers, include, but are not limited to, substituted or unsubstituted dimethicone/copolyol crosspolymer, dimethicone and dimethicone/PEG-10/15 crosspolymers, substituted or unsubstituted dimethicone/polyglyceryl crosspolymer, dimethicone and dimethicone/polyglycerin-3 crosspolymer. Such suitable emulsifying crosslinked siloxane elastomers are sold or made, for example, under the names of "KSG-210" a polyether-modified cross polymer with an INCI name of dimethicone (and) dimethicone/PEG-10/15 crosspolymer, and "KSG-710" a polyglycerin-modified crosspolymer with an INCI name of dimethicone (and) dimethicone/polyglycerin-3 crosspolymer, both available from Shin-Etsu Silicones of America, Inc. (Akron, Ohio).

Co-Emulsifier

The oil phase present in the composition according to the disclosure may optionally include a co-emulsifier at a concentration by weight of about 0.01% to about 1%, or alternatively about 0.05% to about 0.9%, or alternatively about 0.07% to about 0.8%, based upon the total weight of the composition. If the co-emulsifier concentration exceeds 1% by weight of the anti-aging composition, then the composition may still form an emulsion but the desirable transformative effect of cream changing to droplets upon application of shear is not achieved.

Suitable examples of co-emulsifiers include polyether substituted linear or branched polysiloxane copolymers. One preferred co emulsifier is PEG-10 dimethicone available under the tradename of ES-5612 from Dow Corning Corporation (Midland, Mich.), or KF-6017 from Shin-Etsu (Akron, Ohio). Another preferred co-emulsifier is dimethicone (and) PEG/PPG-18/18 dimethicone available under the tradename of ES-5226 DM from Dow Corning Corporation (Midland, Mich.). Other suitable co emulsifiers include, PEG-9 polydimethylsiloxyethyl dimethicone available under the tradename KF-6028 and PEG-9, lauryl PEG-9 polydimethylsiloxyethyl dimethicone available under the tradename KF-6038, both available from Shin-Etsu (Akron, Ohio). Another suitable example of a co-emulsifier is polyoxyalkylene copolymers also known as silicone polyethers. Polyoxyalkylene copolymers are described in detail in U.S. Pat. No. 4,268,499, which is incorporated herein by reference in its entirety. A particularly preferred polyoxyalkylene copolymer is known by its CTFA designation as dimethicone copolyol. A particularly preferred form of dimethicone copolyol is supplied by Dow Corning as DC5225C.

Optional Powders

The composition of the present disclosure may optionally include powders. The optional powders provide formulas that are smoother and softer on the skin.

Representative powders include, but are not limited to talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polystyrene powder, silk powder, crystalline cellulose, starch, titanated mica, iron oxide titanated mica, bismuth oxychloride, and the like. Additional powders include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. A representative powder includes, for example, polymethylsilsesquioxane. Powders may be present in the compositions in amounts generally ranging from about 0.1% to about 10% by weight, based on the total weight of the composition.

Phase Ratio

The phase ratio is calculated by dividing the total weight of the aqueous phase by the total weight of the oil phase. The anti-aging composition of the present disclosure as a water-in-oil emulsion has a ratio by weight of the aqueous phase to oil phase of from about 3.0 to about 12, or alternatively about 4 to about 10, or alternatively about 5 to about 9. The phase ratio excludes any additional optional powders that may be added to the composition. Without intending to be bound by theory, this phase ratio is believed to be critical to (1) the stability of the emulsion in view of the high concentration of water-soluble ingredient(s) contained therein, and (2) the formation of droplets upon application of force onto the emulsion.

Water-Releasing Effect

With respect to the present invention, a good water-releasing effect of the water-in-oil emulsion means that the water-releasing effect has an evaluation result of more than or equal to a score of 3 in the evaluation system described below. The test method and evaluation score of the test system are described below.

About 0.2 g of a water-in-oil emulsion sample of cosmetic composition is taken and placed on the back of a hand, then it is applied thereon by circling gently with the middle finger and ring finger of the other hand, and then the phenomenon of the water-releasing effect is observed when the circling application reaches 20 cycles, and evaluated by a 5-level scoring system. A score of 5 represents that more than 10 bead-like water drops having an average diameter of more than or equal to 3 mm appear, or more than 20 bead-like water drops having an average diameter of more than or equal to 1 mm appear. A score of 4 represents that 2-10 bead-like water drops having an average diameter of more than or equal to 3 mm appear, or 10-20 bead-like water drops having an average diameter of more than or equal to 1 mm appear and the bead-like water drops having an average of more than or equal to 3 mm are no more than 10. A score of 3 represents that 2-9 bead-like water drops having an average diameter of more than or equal to 1 mm appear and there is at most 1 bead-like water drop having an average diameter of more than or equal to 3 mm, or 10-20 bead-like water drops having an average diameter of 1 mm appear. A score of 2 represents that 2-9 bead-like water drops having an average diameter of 1 mm appear. A score of 1 represents that no water drop appears. Each level between scores 5 to 4, 4 to 3, 3 to 2, and 2 to 1 shows that the water-releasing effect is between the two end values described above, and the lower the score, the poorer the water-releasing effect.

In one embodiment, the water-releasing effect of the cosmetic composition of the present disclosure is about 3 to 5.

EXAMPLES

The method of making each of the examples provided in Tables 1 and 2 is generally the same. The examples in Tables 1 and 2 include inventive examples of emulsions with incorporation of high concentrations of water-soluble active ingredients having a water-releasing effect. The examples in Tables 3 and 4 are comparative examples illustrating the lack of emulsion stability and/or stabilization of active ingredients in a typical water-in-oil emulsion.

In each example (inventive and comparative), the viscosity of the emulsion is measured using a Brookfield Viscometer, using Heliopath spindle T-D and speed set at 10 rpm. The spindle was allowed to oscillate in the test sample, and the measurements were taken after one minute.

The water-releasing effect of each example is measured by placing about 0.2 g of the cosmetic composition on the back of a hand, then applying thereon by circling gently with the middle finger and ring finger of the other hand. The phenomenon of the water-releasing effect is observed when the circling application reaches 20 cycles.

Microscopic images of the emulsion were captured to monitor the stabilization of the water-soluble ingredients in the emulsion. The Microscope is set at 10 time magnification, using a Leica DM2500 microscope and analyzed with the Leica Application Suite software.

All examples were monitored for emulsion stability and the stabilization of active ingredients for a period of 8 weeks at 5° C., 25° C., 37° C. and 45° C. and after 10 cycles of freeze/thaw (ranged from −20° C. to 25° C.) Viscosity and microscopic pictures were taken at weeks 4 and 8 by measuring at 25° C.

TABLE 1

Inventive Examples

| Phase | INCI Name | Ex. 1 | Ex. 2 | Ex. 3 | Ex. 4 | Ex. 5 |
|---|---|---|---|---|---|---|
| A | DIMETHICONE/PEG-10/15 CROSSPOLYMER | 1.25 | 1.25 | 1.25 | 1.25 | 0.75 |
| A | DIMETHICONE/POLYGLYCERIN-3 CROSSPOLYMER | | | | | 0.5 |
| A | PEG-10 DIMETHICONE | 0.1 | 0.1 | 0.1 | 0.1 | 0.1 |
| A | DIMETHICONE (and) DIMETHICONOL (88/12) | 1 | 1 | 1 | 1 | 1 |
| A | DIMETHICONE | 13.7 | 13.7 | 13.7 | 13.7 | 13.7 |
| B | WATER, PRESERVATIVES | QS 100 | QS 100 | QS 100 | QS 100 | QS 100 |
| B | NIACINAMIDE | 5 | | 5 | | |
| B | CAFFEINE | 5 | | 5 | | |
| B | *ENGELHARDTIA CHRYSOLEPIS* LEAF EXTRACT | 0.5 | | | | |
| B | FERULIC ACID | 0.5 | | | | |
| B | 3-O-ETHYL ASCORBIC ACID | | 1 | 5 | | |
| B | HYDROXYPHENOXY PROPIONIC ACID | | | 1 | | |
| B | ELLAGIC ACID | | | | 0.01 | |
| B | CETEARETH-25 (and) GLYCERIN (and) CETYL ALCOHOL (and) CERAMIDE NP (and) BEHENIC ACID (and) CHOLESTEROL (and) CERAMIDE NS (and) CERAMIDE EOP (and) CERAMIDE EOS (and) CERAMIDE AP (and) CAPROOYL PHYTOSPHINGOSINE (and) CAPROOYL SPHINGOSINE | | | | 0.14 | |
| B | HYDROXYETHYLPIPERAZINE ETHANE SULFONIC ACID | | | | 1 | |
| B | HYDROXYPROPYL TETRAHYDROPYRANTRIOL | | | | 3.3 | |
| B | MANNOSE | | | | | 10 |
| B | SALICYLIC ACID | | | | | 2 |
| B | ALCOHOL DENAT. | | | | | 5 |
| B | GLYCERIN | 3 | 3 | 3 | 3 | 3 |
| B | SODIUM CITRATE | 0.2 | 0.2 | 0.2 | 0.2 | 0.2 |
| B | SODIUM CHLORIDE | 0.5 | 0.5 | 0.5 | 0.5 | 0.5 |
| B | CITRIC ACID | | | 0.2 | 0.2 | 0.2 |
| C | POLYMETHYLSILSESQUIOXANE | 1 | 1 | 1 | 1 | 1 |
| | Total (%) | 100 | 100 | 100 | 100 | 100 |
| | Brookfield Viscosity (cp) | 38,400 | 65,000 | 55,500 | 28,000 | 45,600 |
| | Total Oil Phase (%) | 12.27 | 12.07 | 12.07 | 12.07 | 12.07 |
| | Total Water Phase (%) | 86.43 | 86.93 | 86.93 | 86.93 | 86.93 |
| | Ratio (Water Phase/Oil Phase) | 7.04 | 7.20 | 7.20 | 7.20 | 7.20 |
| | Water Releasing Effect | 5 | 4 to 5 | 4 to 5 | 4 to 5 | 5 |
| | Texture/Appearance | | Translucent to opaque, gel-like cream. Water droplets released upon rubbing. | | | |
| | Stability Results | | Emulsion remained stable after 8 weeks. No crystals formed. | | | |

TABLE 2

Inventive Examples

| Phase | INCI Name | Ex. 6 | Ex. 7 | Ex. 8 | Ex. 9 | Ex. 10 |
|---|---|---|---|---|---|---|
| A | DIMETHICONE/PEG-10/15 CROSSPOLYMER | 1.25 | 1.25 | 1.25 | 1.25 | 1.25 |
| A | PEG-10 DIMETHICONE | 0.1 | | 0.1 | | 0.07 |
| A | LAURYL PEG-9 POLYDIMETHYL-SILOXYETHYL DIMETHICONE | | 0.1 | | 0.1 | |
| A | DIMETHICONE | 10.7 | 10.7 | 10.7 | 10.7 | 10.7 |

TABLE 2-continued

Inventive Examples

| Phase | INCI Name | Ex. 6 | Ex. 7 | Ex. 8 | Ex. 9 | Ex. 10 |
|---|---|---|---|---|---|---|
| A | TOCOPHEROL | 0.2 | | | | |
| B | WATER, PRESERVATIVES | QS 100 | QS 100 | QS 100 | QS 100 | QS 100 |
| B | ADENOSINE | 0.6 | | | | |
| B | *SCUTELLARIA BAICALENSIS* ROOT EXTRACT | | 0.1 | 0.5 | 0.5 | |
| B | CAFFEINE | 1 | 1 | 5 | | |
| B | NIACINAMIDE | 1 | 1 | 5 | | |
| B | CAPRYLOYL SALICYLIC ACID | 0.1 | 0.1 | 0.1 | 0.1 | |
| B | RESVERATROL | | | | 0.5 | |
| B | GLYCERIN | 15 | 15 | 15 | 15 | 3 |
| B | DIHYDROXYACETONE | | | | | 5 |
| B | PROPANEDIOL | 5 | 5 | | 5 | |
| B | PROPYLENE GLYCOL | | | 5 | | |
| B | DISODIUM EDTA | 0.1 | 0.1 | 0.1 | 0.1 | 0.1 |
| B | SODIUM CITRATE | 0.2 | 0.2 | 0.2 | 0.2 | 0.2 |
| B | SODIUM CHLORIDE | 0.8 | 0.8 | 0.8 | 0.8 | 0.5 |
| B | ALCOHOL DENAT. | 3 | 3 | 3 | 3 | |
| B | CITRIC ACID | | | | | 0.2 |
| B | CARAMEL | | | | | 0.03 |
| B | RED 4 | | | | | 0.0002 |
| C | SILICA SILYATE | 0.7 | 0.5 | 0.5 | 0.5 | |
| | Total (%) | 100 | 100 | 100 | 100 | 100 |
| | Brookfield Viscosity (cp) | 38,500 | 37,000 | 35,000 | 36,000 | 53,600 |
| | Total Oil Phase (%) | 16.8 | 16.6 | 16.6 | 16.6 | 12.07 |
| | Total Water Phase (%) | 83.2 | 83.4 | 8.4 | 83.4 | 87.93 |
| | Ratio (Water Phase/Oil Phase) | 4.50 | 5.02 | 5.02 | 5.02 | 7.29 |
| | Water Releasing Effect | 4 | 3 to 4 | 4 | 3 to 4 | 4 to 5 |
| | Texture/Appearance | | Translucent to opaque, gel-like cream. Water droplets released upon rubbing. | | | |
| | Stability Results | | Emulsion remained stable after 8 weeks. No crystals formed. | | | |

In making each of the inventive examples in Table 1 and 2, the following procedure is used. The ingredients of Phase A (oil phase) were placed in a main beaker and were mixed well with a propeller mixer at about 600-700 RPM and set aside. The ingredients of Phase B (aqueous) were mixed together in a side beaker with a propeller mixer at about 600-700 RPM until all solids were dissolved, giving a clear solution. If needed, Phase B (aqueous) was gently heated to about 40-45° C. until all solids were dissolved. The mixture of aqueous phase ingredients (Phase B) was slowly added to the mixed ingredients of Phase A (oil phase) using a propeller mixer over a period of 10-15 minutes for an about 1 kg batch. As the viscosity of the mixture increased, the stirring speed was increased from 700 rpm to about 1200 rpm. As the aqueous phase is mixed into the oil phase a water-in-oil emulsion was formed. The powders of phase C were added to the batch and were mixed into the water-in-oil emulsion.

TABLE 3

Comparative Example

| Phase | INCI Name | Ex. 11 |
|---|---|---|
| A | PEG/PPG-18/18 DIMETHICONE | 1.75 |
| A | DIMETHICONE | 20.75 |
| B | WATER, PRESERVATIVES | QS 100 |
| B | *SCUTELLARIA BAICALENSIS* ROOT EXTRACT | 0.4 |
| B | CAFFEINE | 5 |
| B | NIACINAMIDE | 5 |
| B | GLYCERIN | 10 |
| B | PROPYLENE GLYCOL | 10 |
| B | DIPROPYLENE GLYCOL | 10 |
| B | DISODIUM EDTA | 0.1 |
| B | SODIUM CHLORIDE | 2 |
| C | ALCOHOL DENAT. | 5 |
| | Total (%) | 100 |
| | Brookfield Viscosity (cp) | 66,000 |
| | Total Oil Phase (%) | 22.5 |
| | Total Water Phase (%) | 77.5 |
| | Ratio (Water Phase/Oil Phase) | 3.44 |
| | Water Releasing Effect | 1 |
| | Texture/Appearance | Light yellow, translucent cream-gel. No water droplets released upon rubbing. |
| | Stability Results | Emulsion remained stable after 8 weeks, but needle-shaped crystals formed on surface of the emulsion. |

In making Example 11 Table 3, the following procedure is used. The ingredients of Phase A (oil phase) were placed in a main beaker and were mixed well with a propeller mixer at about 600-700 RPM and set aside. The ingredients of Phase B (aqueous) were mixed together in a side beaker with a propeller mixer at about 600-700 RPM until all solids were dissolved, giving a clear solution. If needed, Phase B (aqueous) was gently heated to about 40-45° C. until all solids were dissolved. The mixture of aqueous phase ingredients (Phase B) was slowly added to the mixed ingredients of Phase A (oil phase) using a propeller mixer over a period of 10-15 minutes for an about 1 kg batch. As the viscosity of the mixture increased, the stirring speed was increased from 700 rpm to about 1200 rpm. As the aqueous phase is mixed into the oil phase, a water-in-oil emulsion was formed. Lastly, alcohol (Phase was added to the emulsion.

TABLE 4

Comparative Example

| Phase | INCI Name | Ex. 12 |
|---|---|---|
| A | DIMETHICONE/PEG-10/15 CROSSPOLYMER | 1 |
| A | DIMETHICONE (and) DIMETHICONOL (88/12) | 1 |
| A | DIMETHICONE | 9 |
| A | TRISILOXANE | 16 |
| B | WATER | QS 100 |
| B | PHENOXYETHANOL | 0.6 |
| B | CAPRYLYL GLYCOL | 0.2 |
| B | HEXYLENE GLYCOL | 0.1 |
| B | IODOPROPYL CARBAMATE | 0.01 |
| B | POLYAMINOPROPYL BIGUANIDE | 0.04 |
| B | BUTYLENE GLYCOL | 2 |
| B | GLYCERIN | 10 |
| B | SODIUM CITRATE | 0.5 |
| | Total (%) | 100 |
| | Brookfield Viscosity (cp) | 5,000 |
| | Total Oil Phase (%) | 27 |
| | Total Water Phase (%) | 73 |
| | Ratio (Water Phase/Oil Phase) | 2.70 |
| | Water Releasing Effect | 1 |
| | Texture/Appearance | Translucent, milky serum. Watery on skin upon application. No water droplets released upon rubbing. |
| | Stability Results | Emulsion separated after 3 days of freeze-thaw cycles |

In making Example in Table 4, the following procedure is used. The ingredients of Phase A (oil phase) were placed in a main beaker and were mixed well with a propeller mixer at about 600-700 RPM and set aside. The ingredients of Phase B (aqueous) were mixed together in a side beaker with a magnetic stirring bar until all solids were dissolved, giving a hazy solution. The mixture of aqueous phase ingredients (Phase B) was slowly added to the mixed ingredients of Phase A (oil phase) using a propeller mixer over a period of 10-15 minutes for an about 1 kg batch. As the viscosity of the mixture increased, the stirring speed was increased from 700 rpm to about 1000 rpm. As the aqueous phase is mixed into the oil phase a water-in-oil emulsion was formed.

Comparative Example 12, in contrast to the present disclosure, had a total weight percentage of the aqueous phase or water phase of about 73% and a total weight percentage of oil of about 27%, making the ratio of the aqueous phase to oil phase about 2.7. Comparative Example 12 formed a translucent, milky serum that is watery on skin upon application. Comparative Example 12 has no water-releasing effect.

Comparative Example 12 is generally unstable. The microscopic image showed that the water-in-oil emulsion boundary had a leaking boarder, indicating potential instability of emulsion. Though the serum of comparative Example 12 initially formed as an emulsion, after 3 days of freeze-thaw cycles, the serum completely separated.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A composition comprising:
  an aqueous phase containing at least one water-soluble active ingredient at a concentration, by weight, of from about 0.1% to about 20%, based upon weight of the composition; and
  an oil phase consisting of:
    dimethicone, at a concentration, by weight, of from about 1% to about 25%, based upon weight of the composition;
    an emulsifying crosslinked siloxane elastomer at a concentration, by weight, of about 0.1% to about 20%, based upon weight of the composition, the emulsifying crosslinked siloxane elastomer selected from the group consisting of dimethicone/PEG-10/15 crosspolymer, dimethicone/polyglycerin-3 crosspolymer, and a combination thereof; and
    at least one of:
      a co-emulsifier selected from the group consisting of lauryl PEG-9 polydimethylsiloxyethyl dimethicone, PEG-10 dimethicone, and a combination thereof;
      tocopherol; and
      a mixture of dimethicone and dimethiconol;
  wherein a phase ratio of the aqueous phase to the oil phase is about 5 to about 9; and
  wherein the composition converts from an emulsion to a plurality of droplets upon application of shear.

2. The composition of claim 1, wherein the water-soluble active ingredient is chosen from flavones, stilbenoids, tannins, phenolic acids, polyphenolics, vitamins, xanthines, ceramides, cholesterols, sphingosines, C-glycosides, zwitterionic N-substituted amino sulfonic acid buffers, sugars, nucleic acids, α- and β-hydroxy acids, aminopropyl triethoxysilane, dihydroxyacetone, botanical extracts, amino acids, peptides, and combinations thereof.

3. The composition of claim 2, wherein the at least one water-soluble active ingredient is chosen from phenolic or polyphenolic compounds, and combinations thereof.

4. The composition of claim 3, wherein said phenolic or polyphenolic compound is baicalin.

5. The composition of claim 1, wherein the emulsifying crosslinked siloxane elastomer is dimethicone/PEG-10/15 crosspolymer.

6. The composition of claim 1, wherein the emulsifying crosslinked siloxane elastomer is dimethicone/polyglycerin-3 crosspolymer.

7. The composition of claim 1, wherein the composition further includes at least one hydrotrope.

8. The composition of claim 7, wherein the hydrotrope is selected from nicotinamide, caffeine, sodium PCA, sodium salicylate, urea, or hydroxyethyl urea.

9. The composition of claim 7, wherein the hydrotrope is present in the composition in an amount of from about 0.1% to about 20% by weight, based on the weight of the composition.

10. The composition of claim 7, wherein the hydrotrope is present in the composition in an amount of from about 0.5% to about 10% by weight, based on the weight of the composition.

11. The composition of claim 1, wherein the co-emulsifier is at a concentration, by weight, of about 0.01% to about 1%, based upon weight of the composition.

12. The composition of claim 1, further including a powder at a concentration by weight of from about 0.1% to about 5%, based upon weight of the composition.

13. A composition comprising:
(a) an aqueous phase including at least one water-soluble active ingredient chosen from baicalin, ferulic acid, adenosine, resveratrol, ascorbic acid, and hydroxypropyl tetrahydropyrantriol at a concentration, by weight, of from about 0.1% to about 10%, based upon weight of the composition, wherein the aqueous phase is at a concentration, by weight, of from about 80% to about 90%, based upon weight of the composition; and
(b) an oil phase consisting of:
dimethicone at a concentration, by weight, of from about 4% to about 20%, based upon weight of the composition;
an emulsifying crosslinked siloxane elastomer at a concentration, by weight, of about 0.5% to about 10%, based upon weight of the composition, the emulsifying crosslinked siloxane elastomer selected from the group consisting of dimethicone/PEG-10/15 crosspolymer, dimethicone/polyglycerin-3 crosspolymer, and a combination thereof; and
at least one of:
a co-emulsifier selected from the group consisting of lauryl PEG-9 polydimethylsiloxyethyl dimethicone, PEG-10 dimethicone, and a combination thereof;
tocopherol; and
a mixture of dimethicone and dimethiconol; and
(c) at least one hydrotrope chosen from nicotinamide and caffeine, at a concentration, by weight, of from about 0.5% to about 10% by weight;
wherein the composition converts from an emulsion to a plurality of droplets upon application of shear, and
wherein a phase ratio of the aqueous phase to the oil phase is about 5 to about 9.

14. A process for reducing signs of aging on a keratinous substrate comprising the steps of:
(1) applying the composition of claim 1 onto the keratinous substrate; and
(2) applying shear onto the composition, thereby transforming the composition into a plurality of droplets containing at least one water-soluble ingredient that is forced into the keratinous substrate.

* * * * *